United States Patent [19]

Sanderson et al.

[11] Patent Number: 4,722,726
[45] Date of Patent: Feb. 2, 1988

[54] METHOD AND APPARATUS FOR IONTOPHORETIC DRUG DELIVERY

[75] Inventors: John E. Sanderson, North Miami; Stanton R. Deriel, Pembroke Pines, both of Fla.

[73] Assignee: Key Pharmaceuticals, Inc., Miami, Fla.

[21] Appl. No.: 828,794

[22] Filed: Feb. 12, 1986

[51] Int. Cl.$^4$ .............................................. A61N 1/30
[52] U.S. Cl. ...................................... 604/20; 128/798; 128/799
[58] Field of Search ............... 604/20, 891, 892, 896, 604/897; 128/783, 798, 803, 799

[56] References Cited

U.S. PATENT DOCUMENTS

| | | | |
|---|---|---|---|
| 3,677,268 | 7/1972 | Reeves | 604/20 |
| 3,848,600 | 11/1974 | Patrick, Jr. et al. | 128/783 |
| 4,140,122 | 2/1979 | Kühl et al. | 604/891 |
| 4,141,359 | 2/1979 | Jacobsen et al. | 604/20 |
| 4,406,658 | 9/1983 | Lattin et al. | 604/20 |
| 4,416,274 | 11/1983 | Jacobsen et al. | 604/20 |
| 4,419,092 | 12/1983 | Jacobsen et al. | 604/20 |
| 4,465,074 | 8/1984 | Buchalter | 128/803 |
| 4,526,176 | 7/1985 | Bremer et al. | 128/803 |
| 4,557,723 | 12/1985 | Sibalis | 604/20 |

Primary Examiner—C. Fred Rosenbaum
Assistant Examiner—Mario Costantino
Attorney, Agent, or Firm—Richard C. Billups; James R. Nelson; Stephen I. Miller

[57] ABSTRACT

A device for iontophoretic delivery of active ingredient to a patient, that includes an electrode, a first cavity for holding a solution of at least partially active ingredient in ionizing form to be delivered to a patient, a member for maintaining a solution in the first cavity while allowing passage of active ingredient from the first cavity, and an ion exchange member separating the electrode and the first cavity for inhibiting the flow of ions having a charge similar to the charge of the ionized form of the active ingredient from the electrode means to the first cavity is disclosed. A method for iontophoretic delivery of active ingredients to a patient is also disclosed.

25 Claims, 3 Drawing Figures

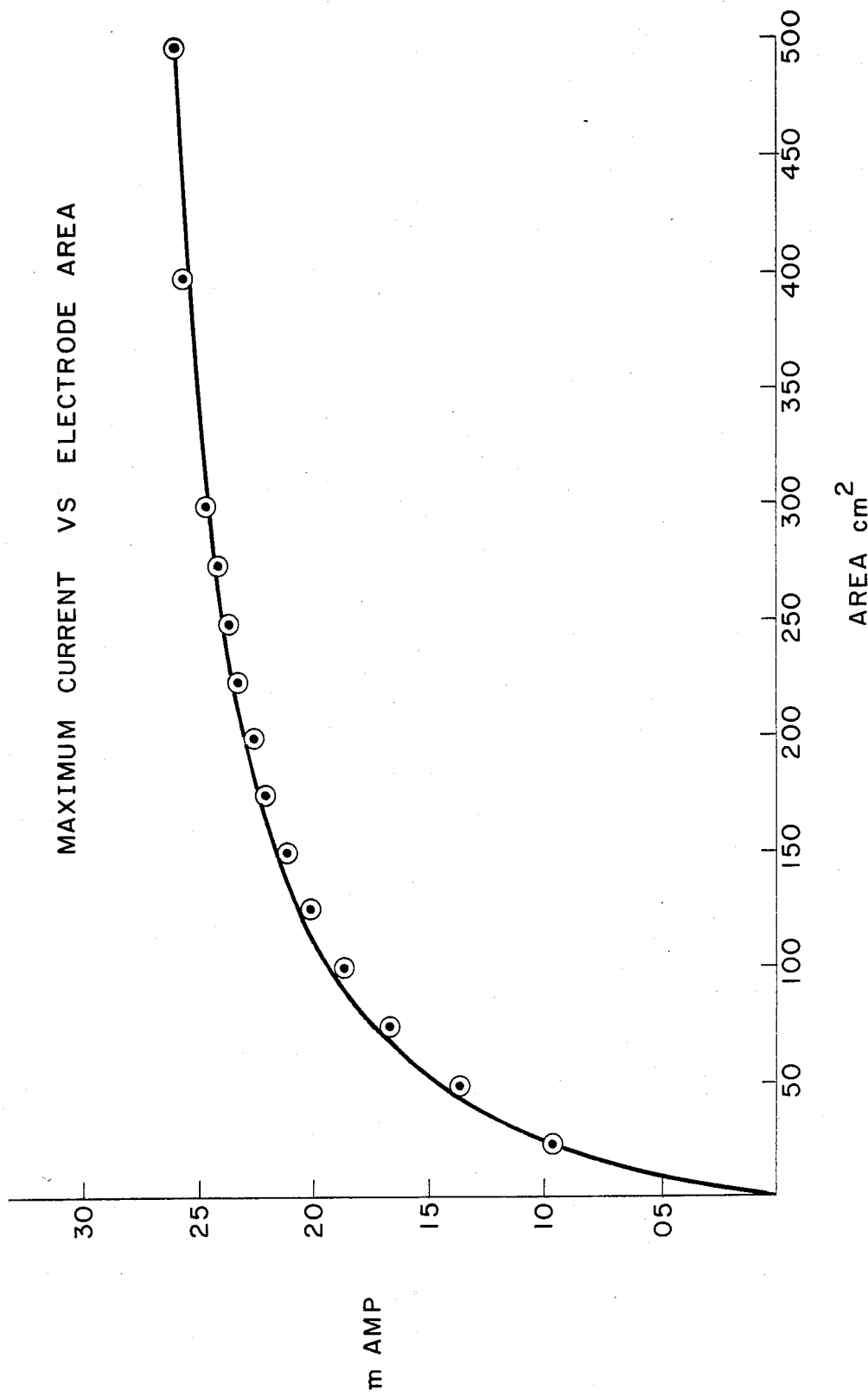

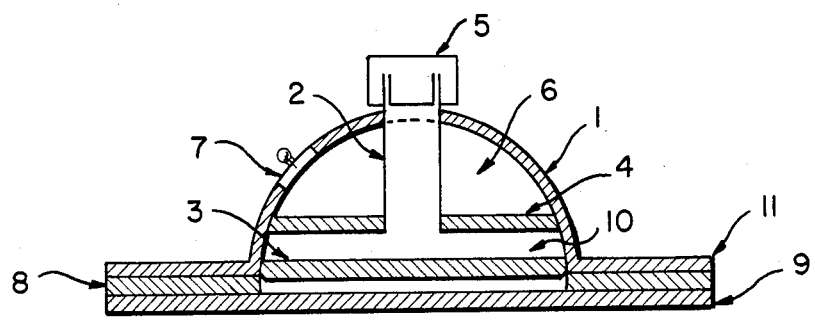
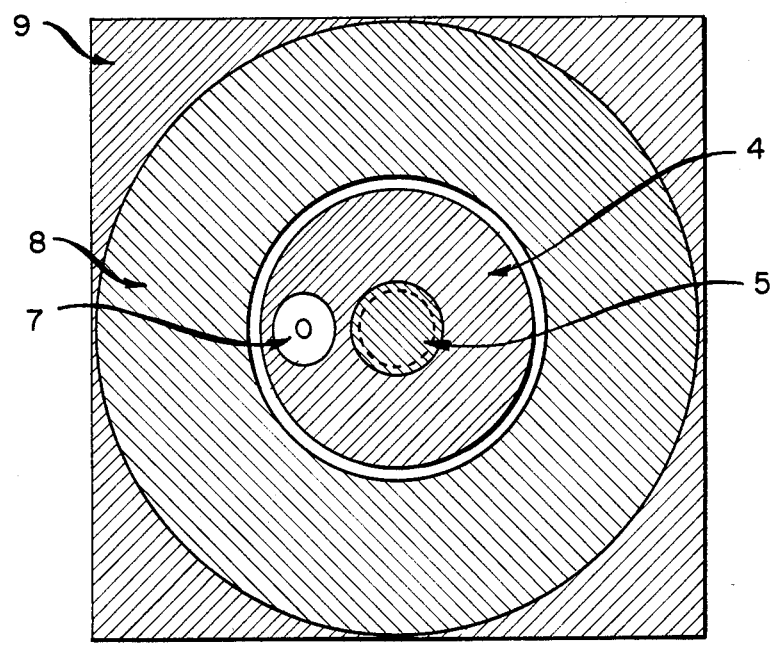

METHOD AND APPARATUS FOR IONTOPHORETIC DRUG DELIVERY

BACKGROUND OF THE INVENTION

The present invention relates to a device for iontophoretic delivery of active ingredients to a patient. The invention also relates to a method for iontophoretic delivery of active ingredients to a patient, and to a method for reducing the possibility of skin trauma caused by iontophoretic delivery of active ingredients to a patient.

Iontophoretic drug delivery is based on the principle that charged molecules will migrate in an electric field toward the electrode of opposite charge. In practice, the process of iontophoretic drug delivery is performed by putting a solution of the drug, often contained in a piece of filter paper or in a gel or in some other device to contain the solution, onto intact skin. The solution is then covered by an electrode. A second electrode is placed elsewhere on the skin, and a direct current source is connected between the two electrodes in such a way that the electrode in contact with the drug solution assumes the same charge as the ionized drug. Under the influence of the electric field present, drug molecules migrate through the skin. A current flows between the electrodes, part of which is carried by the drug.

Although the process of iontophoretic drug delivery may be accomplished using very simple electrodes, certain advantages accrue through the use of more sophisticated electrode configurations. For example, one side effect of the iontophoretic process is the possible formation of vesicles and bullae on the skin beneath the electrodes, as described by W. B. Shelley et al. in J. Invest. Dermatol., 11, pg. 275 (1948). Minimization of this type of skin trauma has been the subject of several recent patents. Jacobsen et al. in U.S. Pat. No. 4,416,274 describe a segmented electrode which is designed to ensure uniform current flow, thereby minimizing skin trauma arising from high localized currents.

In another series of patents, U.S. Pat. Nos. 4,166,457, 4,250,878, and 4,477,971, Jacobsen et al. describe electrodes to which a solution of a drug may be added just prior to the application of the iontophoretic treatment to the patient. The salient feature of these electrodes is that they have an empty chamber closed on the side which is to be attached to the skin by a microporous membrane, which allows the iontophoretic passage of ions but inhibits fluid flow under modest pressure differentials. These electrode designs contain self-sealing devices which allow addition of the drug solution, similar in function to the rubber septa commonly used in medical practice in the manipulation of parenteral solutions. These electrodes employ clothing snaps to provide electrical contact with the external circuit, also a common practice with the use of electrocardiographs and other medical devices which require electrical contact with the skin. One important factor in the use of these electrodes is to ensure that gas bubbles (either from gas originally present in the electrode or from that which is formed by the electrode reaction) do not interfere with the electrical contact between the drug solution and the clothing snap.

Addition of the drug solution to the electrode at the time of application of iontophoretic treatment to the patient provides several advantages. One electrode may be used for delivery of several different drugs. Further, since many of the drugs for which iontophoretic delivery is practical are available in parenteral form, the parenteral form of the drug can often be used without modification.

None of these recent patents concerning the design and construction of iontophoretic electrodes identify or address the problem of pH control in the electrodes. Protons are produced at the anode and hydroxide ions are produced at the cathode by water electrolysis under the usual conditions employed in iontophoretic drug delivery. The ion produced in the drug solution has the same charge as the drug, and if the ion is allowed to accumulate in the solution it will begin to compete with the drug as the treatment proceeds. Another factor which also appears to be pH related is the maximum current density which may be passed through the skin. The maximum current is the maximum current density times the electrode area employed. The penalties for exceeding the maximum permissible current density are pain and burns. Molitor and Fernandez, Am. J. Med. Sci., 198, pg. 778 (1939) reported that the maximum permissible current density is not independent of electrode area. We observe similar behavior. The data from Molitor and Fernandez, on the maximum current which can be applied from an effectively unbuffered but relatively constant pH electrode to the skin for fifteen minutes without causing pain, as a function of area, are shown in FIG. 1. The points are taken from the aforementioned reference. The line of FIG. 1 was derived from a model which says that the pain is derived from the buildup of a substance in the skin, the generation of which is proportional to current and the dissipation of which is proportional to the concentration. The derivation of the equation of the line, fit to the endpoints of the data, is given below. The fit of the data appears to support this hypothesis.

Fick's first law of diffusion:

$$J = K(Cs - Co)$$

$J$ is flux (mass/area time)

$K$ is mass transfer coefficient (length/time)

$Cs$ is source concentration (mass/volume)

$Co$ is sink concentration $$Q = JA$$

$Q$ is total flow (mass/time)

$A$ is area thus $Q = KA(Cs - Co)$ however, $Co$ is $Q/V$ where $V$ is the flow rate in the sink (volume/time)

thus $Q = KACs - KAQ/V$ and $Q = \dfrac{ACsV}{A + V/K}$ defining constants as follows $F = i/Q$ $L = CsVF$ -continued $$M = V/K$$

($i$ is maximum current)

thus $i = AL/(M + A)$

Using the endpoints of the Molitor et al. data (A=25, Q=10 and A=500, Q=26.5) yields a value for L of 29.0 and for M of 47.55. Thus i=29.0A/47.55+A. A comparison of the Molitor et al. experimental values and those calculated from the above equation appear below and are plotted in FIG. 1 as noted above.

| Area cm² | Experimental (m Amps) | Calculated |
| --- | --- | --- |
| 25 | 10.0 | (10.0) |
| 50 | 14.0 | 14.9 |
| 75 | 17.0 | 17.8 |
| 100 | 19.0 | 19.6 |
| 125 | 20.5 | 21.0 |
| 150 | 21.5 | 22.0 |
| 175 | 22.5 | 22.8 |
| 200 | 23.0 | 23.4 |
| 225 | 23.8 | 23.9 |
| 250 | 24.2 | 24.4 |
| 275 | 24.7 | 24.7 |
| 300 | 25.2 | 25.0 |
| 400 | 26.3 | 25.9 |
| 500 | 26.5 | (26.5) |

Time is also a factor affecting the maximum permissible current density. In Table I below is presented the maximum time for an iontophoretic experiment as determined by a drop in skin resistance under a weakly buffered electrode as a function of current density. A significant drop in skin resistance is indicative of skin trauma. Also presented is the total charge passed, which is related to the product of the current and the time.

TABLE I

| Maximum Time for Iontophoresis as a Function of Current | | |
| --- | --- | --- |
| Current | Time | Charge |
| 5.0 mA | 36 min | 10.8 coulombs |
| 2.0 mA | 72 min | 8.6 coulombs |
| 1.5 mA | 110 min | 9.9 coulombs |

At a given current an experiment could only be run for the specified length of time. The time increased with decreasing current in such a way that the product of the two, the total charge, remained relatively constant. Molitor (Merck Report, Jan. 22, 1943) hypothesizes that the factor which limits the current density is the buildup of protons or hydroxyl ions in the subcutaneous tissue as evidenced by a change in pH. Molitor and Fernandez had shown that a change in subcutaneous pH of 1.5 pH units can occur after fifteen minutes of iontophoresis.

This hypothesis is consistent with the data in Table I as well, if one assumes that the reason why the subcutaneous pH beneath an anode drops more or less linearly for fifteen minutes is not that steady state between proton generation and dissipation is reached this slowly, but rather that increase in proton concentration in the subcutaneous tissue is due to increasing proton transport from the donor solution as the buffer capacity of the donor solution is strained by the continuous production of protons at the anode. For example, the data in Table I were generated using physiological saline buffered with 0.01M phosphate. By using 0.5M phosphate as the electrolyte at both electrodes, operation at 2 mA for at least two hours was possible without experiencing a drop in skin resistance. It appears, therefore, that pH control, in addition to being a major factor in optimizing current efficiency, is also a major factor in enabling the use of high current densities and/or long iontophoretic durations without discomfort or skin trauma.

Accordingly, there is a continuing need for an efficient and safe iontophoretic drug delivery device that inhibits the current carrying capacity of ions that compete with the active ingredient.

SUMMARY OF THE INVENTION

A first aspect of this invention is a device for iontophoretic delivery of an at least partially ionized active ingredient through the skin of a patient, comprising:

(a) a first containment means for containing an electrolyte;

(b) an electrode for said first containment means to contact electrolyte in said containment means;

(c) a second containment means, adjacent said first containment means, for containing said active ingredient;

(d) an ion mobility inhibiting means, separating said first containment means from said second containment means, for inhibiting the flow of ions having a like charge as that of the at least partially ionized active ingredient between said first and second containment means; and (e) maintaining means for maintaining the active ingredient in said second containment means while allowing passage of active ingredient ions to the skin of the patient.

The term "electrode" herein is meant to denote a conductive component within the electrode device of the present invention at which, when in contact with electrolyte, oxidation or reduction takes place.

In a second aspect, this invention provides a method for iontophoretic delivery of active ingredient to a patient that includes the steps of applying such a device to the skin surface of the patient, the device containing electrolyte in said first containment means and an effective amount of the active ingredient in said second containment means, applying to the skin surface of the patient a second electrode device spaced from the first device, and supplying current through the electrode devices to cause migration of an effective amount of the active ingredient into the patient.

In a further aspect of this invention, the skin surface of the patient is iontophoretically pre-treated with an anionic surface active agent prior to administration of a cationic active ingredient, or with a cationic surface active agent prior to administration of an anionic active ingredient.

In a further embodiment of the present invention, when the active ingredient is in basic form, it is associated with a pharmaceutically acceptable weak acid. Similarly, when the active ingredient is in acid form, it is associated with a pharmaceutically acceptable weak base. An electrode device may be provided which already contains such active ingredient, ready to use.

In another embodiment, there is provided a method for iontophoretic delivery of active ingredient to a patient comprising applying to the skin surface of the patient an electrode device that includes an electrode and an associated ionized active ingredient, applying to the skin surface of the patient a second electrode device spaced from the first device, and supplying current to the electrode devices to cause migration of a therapeutically effective amount of the active ingredient into the patient, said active ingredient being associated with buffering means. A ready-to-use electrode device may be provided, containing active ingredient and buffering means.

BRIEF DESCRIPTION OF THE DRAWINGS

FIG. 1 is a graph of reported and calculated results as discussed above.

FIG. 2 is a cross sectional view of a device made in accordance with the present invention.

FIG. 3 is a top view of the device of FIG. 2 with domed member not shown to expose the interior parts.

DETAILED DESCRIPTION OF THE INVENTION

In accordance with the present invention, disclosed is an electrode device for iontophoretic delivery of active ingredient to a patient. The device increases the rate and efficiency of drug delivery to the patient. The device also reduces the possibility of skin trauma, including chemical burns caused by uncontrolled production of protons or hydroxide ions at the electrode during iontophoretic delivery of the drug, and electrical burns caused by the use of high currents.

With reference to the drawings, FIG. 2 illustrates a device including a generally conical or domed flanged molding 1, which is made of electrically nonconductive material such as polyethylene or polypropylene. The particular shape is not critical. The opening at the base of the molding may be covered by a microporous membrane 3 which is attached to the bottom of the molding and which is made of electrically nonconductive material, such as stretched polyethylene or polypropylene film. One specific example of such a material is a polypropylene film sold under the trademark Celgard ® 3501 by Celanese, Inc. The membrane can be coated with a surfactant if necessary for the purpose of wettability. The microporous membrane 3 functions to allow electrical migration of ions but inhibits leakage of fluid. The material of which the microporous membrane is made can vary with the active ingredient used in the device. Alternatively, the active ingredient could be maintained in the electrode by providing it in the form of a self-supporting gel. The gel form and the microporous membranes thus are equivalent methods of maintaining the active ingredient in the electrode.

The molding 1 and the microporous membrane 3, together define a chamber that is divided by an ion exchange membrane 4, discussed below, into upper and lower cavities, 6 and 10 respectively, each of which contains a different solution. Thus upper cavity 6 is defined by the upper portion of molding 1 and the membrane 4, while the lower cavity 10 is defined by the lower portion of molding 1 and the ion exchange membrane 4 on top and the microporous membrane 3 on bottom. Good results were obtained with a device having an active area of 15 cm$^2$, with the upper cavity having a volume of 6 ml and the lower cavity a volume of 2 ml. An electrode 7 is provided through the exterior wall of the upper cavity 6 for connection to a current source.

Filling means, typically an injection tube 2, is fitted through an opening in the center of the top of the molding 1, as shown in FIG. 3, so that the upper end of the tube is exposed to the outside of the molding to allow introduction therethrough of drug solution. The tube extends through membrane 4 so that the lower end of the tube is open to the lower cavity. The tube 2 is sealed to the molding at the point where the tube passes through the molding to prevent leakage of fluid out of the upper cavity. The tube 2 is conveniently made of electrically nonconductive material similar to the material of which the molding is made, although the two may be made of different materials.

The upper end of the tube is sealed, preferably by a self sealing means 5. In a preferred embodiment of the invention, the self sealing means is a serum stopper, in which case the self sealing means can be punctured by a hypodermic needle. When the needle is removed, the material of which the sealing means is made closes about and obliterates the opening made by the needle. Such a self-sealing means can also be located in the wall of lower cavity 10, so that the drug can be injected directly into the cavity without the need for an injection tube.

Lower cavity 10 contains an electrolytic solution of an at least partially ionized pharmaceutically active ingredient, and upper cavity 6 contains an electrolyte. The ion exchange membrane 4 inhibits the drug ions and ions of similar charge within the drug solution located in the lower cavity 10 from passing into the upper cavity 6, and inhibits the passage of ions of similar charge from the electrode to the drug solution, thus reducing competition with the drug ions as current carriers. Membrane 4 thus separates the drug solution in lower cavity 10 from the electrode 7 which is in contact with the electrolyte in upper cavity 6. A suitable ion exchange membrane is that sold under the designation AR103-QZL by Ionics, Inc., and under the designations Raipore ® 4010 and 4035 by RAI Research Corp. Generally, the membrane should have as high a selectivity as possible, keeping in mind practical considerations such as the flexibility of the film, which is advantageous for the fabrication of the electrode, and the increase in electrical resistance with the thickness of the membrane. A selectivity of 80%, as determined through 0.5N KCl and 1.0N KCl solutions on different sides of the membrane is useful, although the selectivity may be higher or lower. A buffer, such as a phosphate buffer or ion exchange resin particles, may be used with the electrolyte if desired.

The electrode 7 conveniently can take the form of a clothing snap 7 mounted in the wall of the upper molding so that the stud of the snap is exposed to the outer surface of the molding for connection to an electrical power source, not shown. The base of the snap is exposed to the electrolytic solution within the upper cavity 6, with said solution preferably being gelled and buffered. The electrode could also simply comprise a wire passing through the molding into the electrolyte. An electrode made of stainless steel is desirable if corrosion is a problem.

A flange portion 11 of the molding can also be provided at the base of the device. The flange is coated on its underside with an adhesive layer 8. Any suitable adhesive material can be employed. The adhesive layer serves to secure the device to the skin of the patient during treatment.

A protective release layer 9 may be fixed to the underside of the flange portion 11 by the adhesive layer 8. The release layer 9 protects the microporous membrane 3 from contamination and damage when the device is not being used. When the device is ready for use, the release layer 9 is peeled off to expose the adhesive layer 8 and the microporous membrane 3.

Any standard iontophoretic electrode device may be used as the second electrode device, although the active area should be about the same as that of the first electrode device. Karaya gum is a useful electrolyte for the second electrode device since it can also act as an adhesive, and exhibits some buffering characteristics. Additional buffering may be used if desired.

It has been discovered that the rate of drug delivery generally drops by an order of magnitude when power is shut off, depending specifically on the passive delivery rate of the active ingredient involved. Thus, the present device may be used with a microprocessor and sensor capable of shutting off power when a given drug dose has been administered, particularly when there is a clear physiological indication present, e.g. a given heart rate, when a certain amount has been administered.

It may be desirable to provide the solution of active ingredient with a buffer. The ion of the buffer of like charge or the drug ion should have low ionic mobility. The limiting ionic mobility of this ion is preferably no greater than $1 \times 10^{-4}$ cm$^2$/volt-sec. The buffer can include large multiply-charged ions or weak anion exchange resin or weak cation exchange resin. The buffer ions should have a smaller charge to mass ratio than the active ingredient. The pK of the weak anion exchange resin should be in the range of about 4 to about 7, preferably about 6. Desirably, the anionic exchange resin is useful at a pH of 0-7. One example of such a resin is Amberlite ® IRA-45 resin sold by Rohm and Haas. The pK of the weak cation exchange resin should be in the range of about 6 to about 10, preferably about 9. Desirably, the cationic exchange resin is useful at a pH of about 5-14. One example of such a resin is Amberlite ® CG-50 resin. This buffering method can be used with iontophoretic drug delivery electrode devices other than the specific one disclosed herein.

In accordance with another aspect of the present invention, the active ingredient to be iontophoretically administered to the patient is in the form of a weak acid or weak base salt. Among such weak acids are included maleic, acetic and succinic acids and an example of such a base is ammonia. This advantageously reduces the competition of protons and hydroxide ions, thus improving the current efficiency of the active ingredient. This reduction of protons and hydroxide ions allows for delivery of an increased amount of active ingredient without the possibility of skin burns and trauma. These aspects of the invention are useful for any iontophoretic drug delivery process and apparatus, not only the electrode device disclosed herein.

A wide variety of active ingredients may be used in the present invention. Virtually any active ingredient capable of assuming an ionized form is contemplated as useful in the present invention and the active ingredient must be at least partially in ionized form. However, the present invention is particularly useful for drugs of short duration, where frequent and lengthy application is required. Typical examples of such active ingredients include catecholamines such as dobutamine, anticholinesterase agents such as neostigmine, ergot alkaloids, opioids, opioid antagonists, salicylates and scopolamine. Particularly useful are the inotropic compounds disclosed in Tuttle U.S. Pat. No. 4,562,206, incorporated herein by reference. In one preferred embodiment of the present invention the quaternary ammonium salt forms of aminated active ingredients are used, since the quaternary form will not pass across the blood-brain barrier or the placental barrier, and additionally will not ionize to yield protons. The amount of active ingredient in the ionized form in solution is preferably from about 1 to about 5 mg. ionized active ingredient per ml solution. The pH of the solution containing the active ingredient can be from about 3 to about 10.

In accordance with a preferred embodiment of the present invention, the skin surface of a patient is pretreated iontophoretically with a solution of pharmaceutically acceptable surface active agent having a charge opposite to the charge of the active ingredient. This reduces competition from the migration of body tissue ions outward through the skin, allowing for increased current efficiency of iontophoretic drug delivery, and avoiding discomfort and skin trauma to the patient. Pharmaceutically acceptable surface active agents in accordance with the present invention include, but are not limited to, sodium lauryl sulfate, sodium dodecylsarcosinate, cholesterol hemisuccinate, sodium cetyl sulfate, sodium dodecylbenzenesulfonate, sodium dioctylsulfosuccinate, and quaternary ammonium compounds such as cetyl trimethylammonium chloride. It is believed that the surface active agent functions to drive out similarly charged physiological ions, which can carry charge and thus decrease the efficiency of the iontophoretic drug delivery. The surface active agent does not exhibit the mobility of the physiological ions, and thus does not affect the current efficiency as the physiological ions do. This pretreatment also is useful for iontophoretic electrode devices other than that of the present invention.

In use, the release liner 9 is peeled off and the device is attached to the skin of the patient, with the adhesive layer 8 securably contacting the skin. A syringe or other suitable drug delivery means is filled with a volume of drug solution somewhat larger than the volume of the lower cavity, and the needle of the syringe is forced through the serum stopper 5 into the tube 2. The syringe plunger is drawn back to aspirate air from the lower chamber 10, then the drug solution is forcibly transferred through the needle into the tube 2. This process of air aspiration and transfer of solution is repeated until the drug solution in the device completely fills lower cavity 10, and thus completely covers the bottom of the ion exchange membrane 4. The device is then attached to any suitable power supply (preferably DC) by means of the electrode 7. Also attached to the power supply is a second electrode device that is applied to the skin surface of the patient spaced from the first device. The spacing between the first and second electrode devices can be relatively close, as long as the current is prevented from passing from one electrode device to the other without passing through the skin. The electrode devices provide an electric field by which the active ingredient migrates through the microporous membrane 3 and through the skin into the body.

The present invention has been described in connection with a preferred embodiment as shown in FIGS. 2 and 3. It should be understood, however, that such a device could have a wide variety of shapes or structures consistent with the aspects and embodiments of the present invention as hereinabove described. For instance the device could be of a generally flatter profile, in order to minimize size, and can be of any desired shape for application to a particular area of the skin. The two electrode devices can be incorporated into a unitary body, provided that the above-discussed spacing requirements are met. Such an embodiment would then only require one apparatus to be affixed to the patient. As discussed above, the electrolyte of either cavity can be in the form of a liquid or a self-supporting gel. Other embodiments might contain the electrolyte in a sponge member or other absorbent material such as filter paper. The term "cavity" throughout this description is used in its broadest sense as any unfilled space within which the electrolytic media are contained. Such a cavity may in fact be defined by the electrolytic medium itself, if it is in the form of a self-supporting gel or sponge member. Therefore the term cavity is intended to encompass any suitable containment means.

Although the present invention has been described in detail and with specific reference to its preferred embodiments, it will be understood by those skilled in the art that modifications can be made thereto without departing from the spirit and scope thereof.

What is claimed is:

1. An electrode device for iontophoretic delivery of an at least partially ionized active ingredient through the skin of a patient, comprising:
   (a) a first containment means defining a first chamber for containing an electrolyte;
   (b) an electrical connection in electrical contact with said first chamber defined by said first containment means, for electrically contacting an electrolyte within said first chamber;
   (c) a second containment means defining a second chamber for containing an active ingredient in at least partially ionized form and for iontophoretically delivering said at least partially ionized ingredient into the skin of a patient, said second containment means being separated from said first containment means;
   (d) an ion mobility inhibiting means separating said first and second containment means, capable of passing current from the first containment means to said second containment means while inhibiting the flow of electrolytic ions having a charge like that of the at least partially ionized active ingredient from said first containment means into said second containment means and allowing the flow from the second containment means to the first containment means of ions having a charge which is different from the charge of the at least partially ionized active ingredient, said ion mobility inhibiting means being spacially separated from said electrical contact, and
   (e) maintaining means for maintaining the unionized active ingredient within the second cavity, while allowing electrical current and said at least partially ionized active ingredient to pass from said second containment means into the skin of a patient during iontophoretic treatment.

2. The device of claim 1, wherein the ion mobility inhibiting means comprises an ion exchange membrane.

3. The device of claim 1 further comprising electrolyte in said first containment means, said electrolyte further comprising buffering means for neutralizing ions produced at said electrode.

4. The device of claim 1, wherein the electrode is an anode.

5. The device of claim 1, wherein the electrode is a cathode.

6. The device of claim 1, further comprising active ingredient in a solution in said second containment means, said solution further comprising buffering means for the solution, wherein the ions of the buffering means of like charge to the active ingredient have a limited ionic mobility of less than $1 \times 10^{-4}$ cm$^2$/volt-sec.

7. The device of claim 3, wherein the electrolyte means is in the form of a gel.

8. The device of claim 1, further comprising a filling means in communication with said second containment means.

9. A method for iontophoretic delivery of active ingredient to a patient, comprising the steps of:
   (a) applying to the skin surface of the patient a first electrode device as described in claim 1, said device further comprising electrolyte in said first containment means and active ingredient in said second containment means;
   (b) applying to the skin surface of the patient a second electrode device spaced from said first device; and
   (c) supplying current to the electrodes of said first electrode device and said second electrode device to cause migration of an effective amount of the active ingredient into the patient from said first electrode device.

10. The method of claim 9, wherein said first and second electrode devices are housed in a unitary body.

11. The method of claim 9, wherein the skin surface below said first electrode device is pretreated iontophoretically with a solution of a surface active agent, said surface active agent having a charge opposite that of the active ingredient ions.

12. The method of claim 9, wherein the active ingredient is contained in a solution and which further comprises incorporating buffering means into this solution, wherein the ions of the buffering means of like charge to the charge of the active ingredient have a limiting ionic mobility of less than $1 \times 10^{-4}$ cm$^2$/volt-sec.

13. The method of claim 9, wherein the active ingredient is in basic form and is associated with a pharmaceutically acceptable weak acid.

14. The method of claim 13, wherein the pharmaceutically acceptable weak acid is selected from the group consisting of acetic acid, maleic acid, and succinic acid.

15. The method of claim 9, wherein the active ingredient is in acidic form and is associated with a pharmaceutically acceptable weak base.

16. The method of claim 15, wherein the pharmaceutically acceptable weak base is ammonia.

17. A method for iontophoretic delivery of active ingredient which is in either anionic or cationic form to a patient, comprising pretreating the skin with a cationic or anionic surfactant, respectively; iontophoretically delivering said surfactant into the skin of a patient; applying to the skin surface of the patient a first electrode device that includes an electrode and an associated ionized active ingredient, applying to the skin surface of the patient a second electrode device spaced from said first electrode device, and supplying current to the electrode devices to cause migration of an effective amount of the active ingredient into the patient.

18. A method for iontophoretic delivery of active ingredient to a patient, comprising applying to the skin surface of the patient a first electrode device that includes an electrode and an associated ionized active ingredient, applying to the skin surface of the patient a second electrode device spaced from said first electrode device, and supplying current to the electrode devices to cause migration of an effective amount of the active ingredient into the patient, said active ingredient being in basic form and being associated with a pharmaceutically acceptable weak acid.

19. The method of claim 18, wherein the weak acid is selected from the group consisting of maleic acid, acetic acid and succinic acid.

20. A method for iontophoretic delivery of active ingredient to a patient, comprising applying to the skin surface of the patient a first electrode device that includes an electrode and an associated ionized active ingredient, applying to the skin surface of the patient a second electrode device spaced from said first electrode devices, and supplying current to the electrode devices to cause migration of an effective amount of the active ingredient into the patient, said active ingredient being in acidic form and being associated with a pharmaceutically acceptable weak base.

21. The method of claim 20, wherein the weak base is ammonia.

22. A method for iontophoretic delivery of active ingredient to a patient, comprising applying to the skin surface of the patient a first electrode device that includes an electrode and an associated at least partially ionized active ingredient, applying to the skin surface of the patient a second electrode device spaced from said first electrode device, supplying current to the electrode devices to cause migration of a therapeutically effective amount of the active ingredient into the patient, and associating said active ingredient with buffering means, wherein the ions of said buffering means of like charge to the active ingredient have a limiting ionic mobility of less than $1 \times 10^{-4}$ cm$^2$/volt-sec.

23. A method for iontophoretic delivery of an at least partially ionized active ingredient to the skin of a patient, comprising the steps of:
    (a) applying to the skin surface of said patient a first device of claim 1;
    (b) applying to said skin surface a second electrode spaced from said first device; and
    (c) supplying current to said first device and second electrode sufficient to cause migration of an effective amount of the at least partially ionized active ingredient into the skin of said patient from said first electrode device.

24. The method of claim 23 further comprising pretreating the skin below said first electrode device with a surface active agent having a charge opposite to that of the at least partially ionized active ingredient and iontophoretically delivering said surface active agent into the skin of said patient.

25. A method for iontophoretic delivery of an active ingredient which is in either anionic or cationic form to the skin of a patient, comprising:
    (a) pretreating the skin with a cationic or anionic surfactant, respectively;
    (b) iontophoretically delivering said surfactant into the skin of a patient;
    (c) applying to the skin surface a first electrode device of claim 1;
    (d) applying to the skin surface a second electrode spaced from said first electrode device; and
    (e) supplying current to said first electrode device and second electrode to cause migration of an effective amount of the at least partially ionized active ingredient into the skin of said patient.

* * * * *